Figure 1:
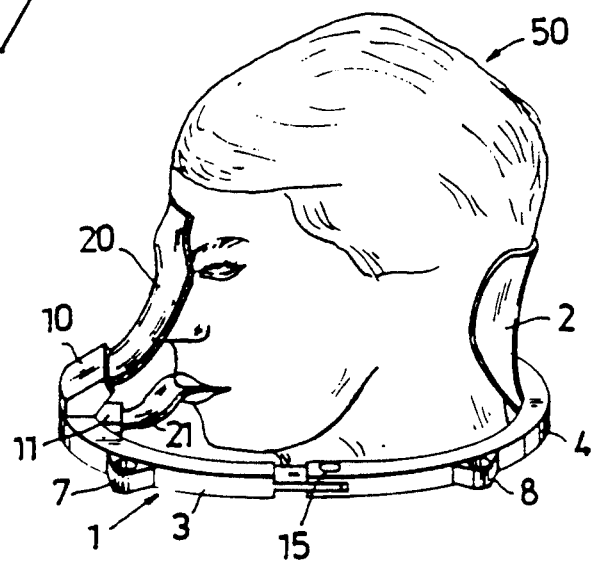

United States Patent [19]

Bergström

[11] Patent Number: 5,040,547

[45] Date of Patent: Aug. 20, 1991

[54] DEVICE FOR REPEATABLE POSITIONING OF A REFERENCE ELEMENT ON A HUMAN HEAD

[75] Inventor: Mats Bergström, Uppsala, Sweden

[73] Assignee: Fixster Instruments AB, Sweden

[21] Appl. No.: 448,680

[22] Filed: Dec. 11, 1989

[30] Foreign Application Priority Data

May 10, 1989 [SE] Sweden ................... 8901701

[51] Int. Cl.⁵ .......... A61F 11/00; A61F 9/00; A61H 1/02; A61C 5/14

[52] U.S. Cl. ............... 128/857; 128/858; 128/75; 128/DIG. 23; 128/861; 128/87 B

[58] Field of Search ............. 128/87 B, 87 C, 869, 128/DIG. 23, 75, 857–861, 863

[56] References Cited

U.S. PATENT DOCUMENTS

| | | | |
|---|---|---|---|
| 1,397,499 | 11/1921 | Brennan | 128/DIG. 23 |
| 2,528,370 | 10/1950 | Johnston | 128/DIG. 23 |
| 3,220,406 | 11/1965 | Connelly | 128/DIG. 23 |
| 3,724,452 | 4/1973 | Nitschke | 128/75 |
| 4,161,946 | 7/1979 | Zuesse | 128/87 B |
| 4,582,051 | 4/1986 | Greene | 128/DIG. 23 |
| 4,793,334 | 12/1988 | McGuinness | 128/87 B |

Primary Examiner—Robert A. Hafer
Assistant Examiner—M Brown
Attorney, Agent, or Firm—Ostrolenk, Faber, Gerb & Soffen

[57] ABSTRACT

A device for repeatable positioning of a reference element on a human head comprises a standardized base in substantially the shape of a ring (1) with a support (2) for abutment against the back of the patient's head, an attachment means (10, 11) located on the ring (1) substantially diametrically opposite to the position of the support (2), an initially deformable first splint (20) detachably fitted in the attachment means (10, 11) and arranged to form a special bite piece for the patient, to be correctly bitten by the patient when the support (2) abuts the back of the head and the nose splint is correctly in contact with the region of root of the patient's nose.

8 Claims, 2 Drawing Sheets

DEVICE FOR REPEATABLE POSITIONING OF A REFERENCE ELEMENT ON A HUMAN HEAD

The present invention relates to a device for repeatable positioning of a reference element on a human head, of the type described in the preamble to claim 1.

When scanning, taking pictures or giving radiation treatment, for instance, of the inside of a human head by means of radiation technique, it is desired to be able to fit a reference element on various different occasions, such as a reference grid, in a position which can be accurately repeated in relation to the patient's head, allowing a specific point to be accurately identified on the different occasions.

It is desired to be able to fit a base for the reference element onto the patient with requisite stability and repeatability without having to secure the base with screws or the like to the skull of the patient.

Previous suggestions for achieving the base have entailed constructing a tightly fitting plastic helmet on the patient's head and then attaching the reference element to this individually constructed plastic helmet. For security, this helmet must be stabilized by side struts resting against the patient's mouth.

The accurate positioning of the plastic helmet on the patient's head is ensured by its partially surrounding the head. However, the helmet must be cut open to allow removal.

The construction of such a plastic helmet is relatively time-consuming, it requires considerable storage space, and the accuracy of its positioning suffers from the helmet having to be made removable. Furthermore, the patient's hair may considerably affect positioning accuracy.

One object of the invention is to offer a device to allow a reference element to be repeatedly borne in the same position on a human head, said device being quick, simple and convenient to prepare and of which the parts specific to a particular patient can be stored in a relatively small space. The device claimed shall also allow the position of the reference element to be accurately repeated without the need for any surgical incision to be performed on the patient.

This object is achieved according to the invention by means of the various embodiments of the device defined in the appended claims.

The invention thus comprises the use of a standardized base structure, suitably in the shape of a ring, which is designed to be placed (generally horizontally) around the patient's neck. The ring has suitably a form and size corresponding to the contour of the head in a normal plane to an axis defined by the patient's neck. The ring is suitably provided with a fixed support for abutment against the back of the patient's head. Diametrically opposite to the support are two attachments on the ring, one for a bite piece and one for a splint resting against the region of the nose root.

The nose and bite splints are detachably applied in the ring attachments. They are initially deformable and can thus be shaped to fit a particular patient. The splints are suitably arranged to be stabilized after being shaped to fit the patient. For this reason the splints are made of a curable material or a thermoplastic material which can be deformed at increased temperature. The splints may be made, for instance, of a known type of plastic which can be heated in hot water, for instance, to make it malleable, and is then sufficiently stabilized after shaping and cooling to remain stable at room temperature.

The base ring is suitably formed from two C-shaped elements detachably connected together, preferably via a hinge on one side and a locking device on the other side to facilitate assembling and dismantling the device with splints applied in the attachments.

The ring is suitably provided with standard attachments for standard reference elements.

The device is fitted initially to a patient by placing the ring with splints applied, on the patient. At this stage the splints are in deformable state. The support on the ring is brought into contact with the back of the patient's head and the bite piece is deformed to fit the patient's bite. The nose splint is also deformed to fit the region of the nose root, i.e. to grip the patient's nasal bone and the edge of the frontal brow bone. The bite portion of the bite splint may then be said to form a first suspension point for the device. The nose splint and support for the back of the head prevent the device from moving forward/backward in the vertical plane in relation to the patient, around the point defined by the bite portion of the bite splint.

The nose splint also fits over the bridge of the patient's nose and the support for the back of the head may be curved to prevent the device from tilting or rotating in a vertical plane in transverse direction. The two splints may generally be relatively wide, flat strips, allowing the bite splint in particular, due to its width, to contribute to preventing tilting of the device in transverse direction. As the nose splint grips around the nose bone, it cannot easily slip in the transverse direction, and the bite splint cannot easily slip in the transverse direction either.

It will be understood that, after being shaped to fit the patient, the two splints will constitute the elements which define an exact orientation and position of the ring on the patient, when assembled on the standardized ring.

The two splints require little storage space and can be kept with previous images of the patient or other information relating to the patient, and a reference element used for one image or examination can easily and quickly be assembled to its original position in relation to the patient's head, using the standard ring and the two splints specific to the patient, so that further images can be taken with the reference element in exactly the same position on the patient's head.

The invention thus offers simple, quick and stable assembly of a reference element on a patient's head without the need for any surgical incision being performed on the patient. The method according to the invention results in only two relatively small elements shaped to fit the patient, i.e. the splints described above. These splints weight very little and require little storage space, thus facilitating their storage. With the aid of these splints shaped to fit the patient, together with the standardized ring and a standard reference element, the reference element can be re-assembled quickly and simply in exactly the same position and with the same orientation as when it was last assembled on the patient. This in turn offers improved opportunities for effectively utilizing the relevant examination equipment, such as a positron camera, expensive X-ray equipment, radiation equipment or the like.

The invention will be described by way of example in the following, with reference to the accompanying drawings.

Figure 2:
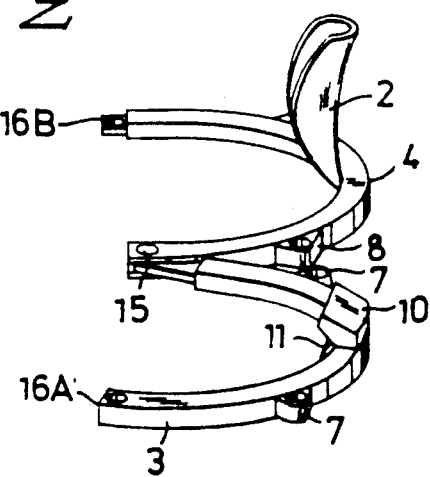
Figure 3:
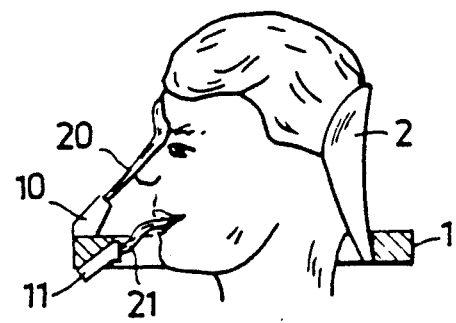
Figure 4:
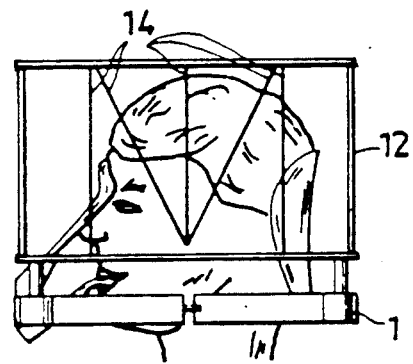
Figure 5:
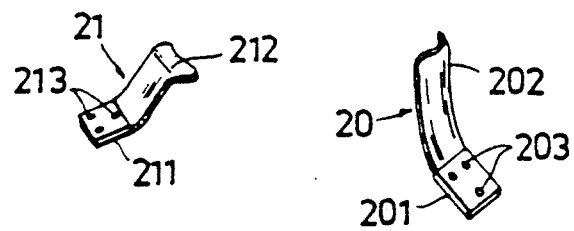

FIG. 1 shows in perspective a device according to the invention, assembled on a patient, FIG. 2 shows the base ring of the device, FIG. 3 shows a vertical section through the device according to FIG. 1, FIG. 4 shows the device with a reference element in place, and FIG. 5 shows in perspective the two splints which form a part of the device.

The embodiment of the device shown in the drawings comprises an oval base ring 1. At one end of the ring 1 is a support 2 for the back of the patient's head 50. At the point on the ring 1 diametrically opposite to the support 2 (i.e. at the top of the oval shape) are attachments 10 and 11 for a nose splint 20 and a bite splint 21.

The ring is formed from two generally C-shaped elements 3, 4 which are preferably joined together via a hinge 15 at one side of the ring and a locking device on the other side, said locking device being formed by locking elements 16a, 16b which fit together at the ends of the element 3, 4.

The ring 1 is provided with attachments allowing a reference element 12 to be detachably assembled thereon. The attachments may be in the form of tubular holders 7, 8 to receive corresponding dowels 17, 18 on the reference element 12.

The reference element 12 is in itself conventional and provided with markings 14 visible on the images to facilitate plotting.

Considering FIG. 5 it can be seen that the bite splint 21 has a base portion 211 to enable connection to attachment 11 on the ring 1, for instance by means of screws passing through the indicated screw holes 213. The bite splint is also provided with a deformable, free end portion 212 designed for shaping to fit the bite produced by the patient's teeth or gums when the bite splint is applied in the ring and the support 2 is firmly in contact with the patient as shown in FIGS. 1 and 2.

FIG. 5 also shows a nose splint 20 with base fitting 201, designed to be attached to the appropriate attachment 10 on the ring 1 by screws, for instance, inserted through the indicated screw holes 203. The nose splint 20 also has a free end 202 which is deformed to fit the region of the root of the nose when the support 2 is in contact with the back of the patient's head and the bite splint 21 is correctly shaped and placed.

FIG. 5 shows the splints 20, 21 after being shaped to fit a patient and the teethmarks can be seen on the bite splint 21.

Initially the splints 20, 21 are attached on the ring and the ring is then applied on the patient, its two halves being closed and secured by the attachment 16. Thanks to the ring 1 being in two parts, the bite portion of the bite splint can easily be inserted in the patient's mouth and the risk of the nose splint 20 inconveniencing the patient during application of the ring 1 is limited. The splints 20, 21 are presumed to be in deformable state since they shall be deformed to fit the patient in question. The splints can preferably be subsequently stabilized in the desired deformed shape. This can be achieved by using a thermoplastic material for the splints and increasing the temperature of the material at the deformation stage. Alternatively the splints may be of a curable material which is cured after the desired deformation. A third alternative is for the splints 20, 21 to have an initially weak structure which is then strengthened after deformation to fit the patient, by means of reinforcing, material coating or the like.

The splints 20, 21 shaped to fit a particular patient require little storage space and may possibly be kept together with other material pertaining to the patient, such as previous X-rays and the like.

When the patient is to be examined again the previously shaped splints can be applied in the ring as shown in FIG. 2, and the ring then applied on the patient by closing the two hinged parts and securing the locking device. The reference frame 12 can then be assembled on the ring 1.

A specific embodiment has been described above by way of example, but it should be obvious that the average person skilled in the art can offer structural variations within the scope of the inventive concept as defined in the appended claims.

The base element as defined by the ring 1 could, for instance, be shaped differently. It might, for instance, be C-shaped, in which case if a hinge 15 is used it should preferably be lockable when the base element is in operative state. The attachments 10, 11 on the base element, as also the attachment fittings 201, 211 on the splints 20, 21, need not necessarily be as shown in the drawing, but may have some other conventional shape offering the intended function, i.e. detachable, stable connection of one end of the splints to the base element 1. The support 2 has been shown with only one curve, but may of course have a double curved form if such concavity is considered to give improved precision in positioning the device on the patient 50.

The invention has been described above in the form of a device. However, the invention also includes the described method of achieving repeatable positioning of a reference element on a human head. The reference element may be permanently secured to the ring.

The term "reference element" relates not only to an element which is visible on images, but may also be a device which directly or indirectly offers alignment of a source of radiation, for instance, such as an attachment on the ring for a radiation source for radiation treatment.

I claim:

1. A device for repeatable positioning of a reference element (12, 14) on a human head (50), comprising a standardized base in substantially the shape of a ring (1), with a support (2) for abutment against the back of a patient's head, an attachment means (10, 11) located on the ring (1) substantially diametrically opposite to the position of the support (2), an initially deformable first splint (20) fitted in the attachment means and arranged to rest against the region of the nose root when the support (2) abuts the back of the head, and a second initially deformable splint (21) fitted in the attachment means and arranged to form a bite piece to be correctly bitten by the patient when the support (2) abuts the back of the head.

2. A device as claimed in claim 1, wherein the first splint (20) and the second splint (21) are detachably fitted in the attachment means to allow separate storage when the device is not fitted on the head.

3. A device as claimed in claim 1, wherein the splints for the patient's bite and nose are made of a curable material which is cured in conjunction with or after the splints have been deformed to fit the patient.

4. A device as claimed in any claim 1 wherein the ring (1) is provided with means (15, 16) permitting the ring to be opened to facilitate applying the ring on the patient.

5. A device as claimed in claim 4, wherein the means comprise a hinge and an openable locking device (16a, 16b) in opposing side portions of the ring (1).

6. A method for repeatably positioning a reference element (12, 14) on a human head, comprising placing a base element (1) in substantially the shape of a ring around the patient's neck, with a support located on said ring in contact with the back of the patient's head, placing an initially deformable bite piece fitted on the ring substantially diametrically opposite the support (2) in the patient's mouth, and causing a nose splint (2) fitted opposite the neck support on the ring (1) to abut the region of the nose root, deforming the parts of the nose splint to lie in surface contact with the region of the nose root, causing the bite piece to be correctly bitten by the patient when the support (2) is in contact with the back of the patient's head, and permanently fixing the splints in the shape thus acquired.

7. A method as claimed in claim 6, wherein the splints (20, 21) are detachably fitted to the ring and are stored separately when not fitted on the patient's head.

8. A method as claimed in claim 7, wherein the base element (1) is standardized, having attachment means (7, 8) for detachable assembly of the reference element (12).

* * * * *